(12) United States Patent
Kennedy

(10) Patent No.: US 10,480,927 B2
(45) Date of Patent: Nov. 19, 2019

(54) OPTICAL COHERENCE TOMOGRAPHY SYSTEM

(71) Applicant: OncoRes Medical Pty Ltd, Nedlands, Western Australia (AU)

(72) Inventor: Brendan Kennedy, Crawley (AU)

(73) Assignee: OncoRes Medical Pty Ltd, Nedlands, Western Australia (AU)

(*) Notice: Subject to any disclaimer, the term of this patent is extended or adjusted under 35 U.S.C. 154(b) by 0 days.

(21) Appl. No.: 16/096,100

(22) PCT Filed: Apr. 28, 2017

(86) PCT No.: PCT/AU2017/050397
§ 371 (c)(1),
(2) Date: Oct. 24, 2018

(87) PCT Pub. No.: WO2017/185145
PCT Pub. Date: Nov. 2, 2017

(65) Prior Publication Data
US 2019/0120608 A1    Apr. 25, 2019

(30) Foreign Application Priority Data
Apr. 29, 2016 (AU) .................. 2016901558

(51) Int. Cl.
*G01B 9/02* (2006.01)
*G01N 21/47* (2006.01)
(Continued)

(52) U.S. Cl.
CPC ........ *G01B 9/02091* (2013.01); *A61B 5/0066* (2013.01); *A61B 5/1459* (2013.01);
(Continued)

(58) Field of Classification Search
CPC ........... G01B 9/02091; G01B 9/02015; G01B 9/02017; G01B 9/02019; G01B 9/02021; G01B 9/020277; G01B 11/161
See application file for complete search history.

(56) References Cited

U.S. PATENT DOCUMENTS

2004/0184038 A1 * 9/2004 Freischlad ............. G01B 11/06
356/512
2007/0109553 A1   5/2007 Feldchtein et al.
(Continued)

FOREIGN PATENT DOCUMENTS

EP     2301423       3/2011
WO     2004073501    9/2004
(Continued)

OTHER PUBLICATIONS

International Search Report for Application No. PCT/AU2017/050397 dated May 17, 2017 (8 pages).

*Primary Examiner* — Jonathan M Hansen
(74) *Attorney, Agent, or Firm* — Michael Best & Friedrich LLP

(57) ABSTRACT

The present disclosure provides an optical coherence tomography (OCT) system for characterising first and second areas of interest of a material. The OCT system comprises first and second optical elements in use positioned at the first and second areas of interest of the material. The first and second optical elements are at least partially transmissive for electromagnetic radiation. The system further comprises first and second scanning heads in use positioned at the first and second optical elements, respectively, to receive electromagnetic radiation that has interacted with the material at the first and second areas of interest. In addition, the system comprises at least one detector optically coupled to the first and second scanning heads. The first and second optical elements are arranged such that respective reference radia-
(Continued)

tion associated with the first and second optical elements is generated by reflection at interfaces of or at the first and second optical elements, respectively, and the first and second optical elements are arranged or positioned such that an optical path length difference between the reference radiation associated with the first optical element reference radiation and electromagnetic radiation that interacted with the material associated with the first optical element differs from an optical path length difference between the reference radiation associated with the second optical element and electromagnetic radiation that interacted with the material associated with the second optical element.

20 Claims, 6 Drawing Sheets

(51) Int. Cl.
*A61B 5/00* (2006.01)
*A61B 5/1459* (2006.01)
*G01B 11/16* (2006.01)

(52) U.S. Cl.
CPC ....... *G01B 11/161* (2013.01); *G01N 21/4795* (2013.01); *A61B 2562/0204* (2013.01)

(56) References Cited

U.S. PATENT DOCUMENTS

| | | | | |
|---|---|---|---|---|
| 2007/0206197 A1* | 9/2007 | Buckland | ............... | A61B 3/102 356/479 |
| 2012/0300213 A1* | 11/2012 | Frankovich | ........ | G01B 11/0675 356/450 |
| 2012/0307255 A1* | 12/2012 | Kim | ................... | G01B 9/02057 356/477 |

FOREIGN PATENT DOCUMENTS

| | | |
|---|---|---|
| WO | 2009120544 | 10/2009 |
| WO | 2012110051 | 8/2012 |
| WO | 2012145133 | 10/2012 |
| WO | 2013148758 | 10/2013 |
| WO | 2013164004 | 11/2013 |
| WO | 2014149839 | 9/2014 |

* cited by examiner

OPTICAL COHERENCE TOMOGRAPHY SYSTEM

FIELD OF THE INVENTION

The present invention broadly relates to an optical coherence tomography system and relates particularly, though not exclusively, to an optical coherence tomography system for characterising biological tissue.

BACKGROUND OF THE INVENTION

Optical Coherence Tomography (OCT) is an optical imaging technique frequently used to image biological tissue and is capable of acquiring high-resolution images. Usually broadband light having a coherence length of 1-10 µm is scanned across an area of interest, typically up to 10 mm×10 mm, to generate an OCT image to depths of 1-3 mm. The light penetrates into material at an area of interest where, dependent on local material properties, a portion of the light is reflected or backscattered. The OCT system combines the reflected or backscattered light with reference light in an interferometer setup, which results in interference between light reflected from the reference and the material if the path length differences are less than the coherence length of the light. By detecting the light backscattered from the sample at a number of different path lengths, a depth resolved image with an imaging depth of 1-3 mm can be obtained.

OCT can be used to identify diseased tissue and may be used to identify, for example, tumours during surgery. However, the available time during surgery is very limited and, using known OCT technology, in many cases, it is not practical to scan multiple areas simultaneously. The characterisation of multiple areas of a material simultaneously using known OCT technologies requires a complex optical design, which is unsuitable for portable implementation.

SUMMARY OF THE INVENTION

In accordance with a first aspect of the present invention, there is provided an optical coherence tomography (OCT) system for characterising first and second regions of interest below first and second surface areas, respectively, of a material, the OCT system comprising:
first and second optical elements in use positioned at the first and second surface areas, respectively, the first and second optical elements being at least partially transmissive for electromagnetic radiation;
a scanning system having first and second optical portions, the first and second scanning portions being positioned at the first and second optical elements, respectively, to receive electromagnetic radiation that has interacted with the material within the first and second regions; and
at least one detector optically coupled to the scanning system;
wherein the first and second optical elements are arranged such that respective reference radiation associated with the first and second optical elements is generated by reflection at interfaces of or at the first and second optical elements, respectively, and the first and second optical elements are arranged or positioned such that an optical path length difference between the reference radiation associated with the first optical element and electromagnetic radiation that interacted with the first region differs from an optical path length difference between the reference radiation associated with the second optical element and electromagnetic radiation that interacted with second region.

The term "material" as used herein is intended to encompass any matter including, for example, biological material such as biological tissue and biomaterials, non-biological material such as silicone material, and other materials such as materials used in the field of geology or materials science.

In one specific embodiment the OCT system is arranged such that both the reference radiation and the electromagnetic radiation that interacted with the material associated with the first optical element and also both the reference radiation and the electromagnetic radiation that interacted with the material associated with the second optical element propagate along a common optical path towards the detector.

The first and second surface areas may be directly adjacent surfaces or may be spaced apart from each other. Further, the first and second regions may be directly below the first and second surface areas, respectively.

In addition, the first and second optical elements may be joined elements or may be separate elements that may or may not be spaced apart.

The first and second optical portions of the scanning system may be provided in the form of first and second scanning heads positioned at the first and second optical elements, respectively, to receive electromagnetic radiation that has interacted with the material at the first and second areas of interest.

Alternatively, the OCT system may comprise a scanning system, such as a single scanning mirror, and may be arranged such that electromagnetic radiation is directed (for example via a beam splitter and mirror) to the first and second optical portions, which may each comprise a suitable optical lens.

In a first specific embodiment of the present invention the first and second optical elements are arranged such that an optical length of a path of the electromagnetic radiation through at least a portion of the first optical element to an interface of or at the first optical element differs from that through at least of portion of the second optical element to an interface of or at the second optical element. In this embodiment the first and second optical elements may be arranged such that an optical length of a path of the electromagnetic radiation through at least a portion of the first optical element to an interface of or at the first optical element differs from that through at least of portion of the second optical element to an interface of or at the second optical element by a length that is longer than the imaging depth of the OCT image of the material under test, such as longer than 1 mm, 2 mm 3 mm or more, which affects the optical path lengths differences between the respective electromagnetic radiation and the respective reference radiation accordingly. Consequently, it is possible to display OCT images for the first and second areas of interest separately even if the reference radiation and the electromagnetic radiation that has interacted with the respective areas of interest propagate along the single common optical path and are detected on a common detector.

The first and second optical elements may have different thicknesses. The first and second optical elements may also have at least portions that have different refractive indices.

Alternatively, the first and second optical elements may have identical refractive indices and different thicknesses. Further, the first and second optical elements may have identical thicknesses and different refractive indices.

The first and second optical elements may be formed from the same, similar or different materials. For example, the first and second optical elements may be formed from glass or a polymeric material or a compliant material such as silicone.

In one embodiment of the present invention, each of the first and second optical elements comprises at least two layers of a material having different optical properties. In this embodiment, the OCT system is arranged such that the electromagnetic radiation that is reflected at an interface between two of the at least two layers of each optical element forms respective reference radiation.

At least one of the layers of the first optical element through which in use the reference radiation propagates may have a thickness and/or a refractive index that is different to that of a corresponding layer of the second optical element.

In an alternative second embodiment the first and second optical elements may or may not be arranged such that an optical length of a path of the electromagnetic radiation through at least a portion of the first optical element to an interface of or at the first optical element differs from that through at least of portion of the second optical element to an interface of or at the second optical element. In this second embodiment the first and second optical elements are arranged or positioned such that an optical path length of electromagnetic radiation that interacted with the material at the first optical element differs from that of the electromagnetic radiation that interacted with the material at the second optical element. For example, the first and second optical elements may in use have respective spacings from the material at the first and second optical elements. Alternatively, the first and second optical elements may comprise respective contact layers having respective optical properties and that in use space the first and second optical elements from the material.

The first and second optical elements may be separate from the first and second optical portions of the scanning system. Alternatively, the first and second optical elements may form a part of, or may be joined with the first and second optical portions of the scanning system, respectively.

In some embodiments of the present invention the OCT system comprises a source of the electromagnetic radiation, the source being optically coupled to the first and second scanning heads.

The source of electromagnetic radiation, the scanning system and the detector may be optically coupled by optical waveguides, such as optical fibres or the light may propagate in free-space. The electromagnetic radiation emitted by the source may be distributed between the first and second optical portions of the scanning system using a suitable optical splitter, such as an optical fibre coupler or a free-space beam splitter.

The material may be one of a plurality of materials. For example, the material may comprise first and second materials that are separate (and may be otherwise different) and the first optical element may be positioned at a first surface area of the first material and the second optical element may be positioned at the second surface area of the second material.

In one specific example the first material may for example be biological tissue of a patient and the second material may be a mirror that is stationary relative to the second optical element and that functions as a reference. It is then possible to determine a motion of the second material relative to the OCT system.

The first and second optical elements may have a non-uniform thickness, such as a tapered thickness and may have a generally wedge-shaped cross-sectional shape. This embodiment provides the advantage that at least some reflection of the electromagnetic radiation at an interface of the layer facing the respective area of interest of the material is not detected by the detector when the respective scanning head is positioned to receive electromagnetic radiation that exits the respective optical element in a direction that largely normal to an exit surface of the respective optical element.

It will be appreciated by a person skilled in the art that embodiments of the present invention are not limited to two regions of interest, of a material, and that the simultaneous acquisition of more than two OCT images for more than two regions of interest of the material is envisaged.

The first and second optical elements may have any suitable cross-sectional shape. The first and second optical elements may have a rectangular, curved or any suitable polygonal cross-sectional shape. For example, the first and second optical element may have a generally flat shape or may be cup-shaped.

In one embodiment of the present invention, the OCT system is used to evaluate a mechanical property of the material in multiple regions of interest, which may be performed simultaneously. In this embodiment, the OCT system is arranged to apply a mechanical load to the first and second regions of interest via the respective first and second surface areas, such as through the first and second optical elements that are in use in contact with the material.

The OCT system may also comprise an elongated probe that is arranged for insertion into biological tissue. The probe may comprise a tubular body and may have at least a region that is transmissive for the electromagnetic radiation. The first and second optical elements may be positioned along a length of the probe at a region or at a window portion of the probe or may form a window portion of the probe. The first optical element may be one of a plurality of first optical elements and/or the second optical element may be one of a plurality of second optical elements. The probe may comprise more than one first optical element and/or more than one second optical element that are positioned along a length of the probe. The optical elements may be positioned along a length portion of the probe at different radial and/or length positions. For example, adjacent optical elements may be separated by a distance of 1 to 3 mm. The OCT system having the probe may be arranged to simultaneously generate multiple images of different regions of the biological tissue adjacent the probe. In this embodiment, the probe typically is a rotatable probe such that scanning of the area of interest can be performed by rotating the probe.

The OCT system may be arranged to determine stress and/or strain within a portion of the material such that the mechanical property of the material can be evaluated using the determined stress and/or strain within the portion of material at the first and second areas of interest in sequence or simultaneously.

The OCT system may comprise an actuator, or other mechanism, for applying a load. The actuator may be a piezoelectric actuator. Further, the OCT system may comprise sensing layers having known mechanical properties, such as layers that comprise a silicone material. Each sensing layer may in use be positioned between a respective optical element and the area of interest. Alternatively, each sensing layer may form a portion of a respective optical element.

The OCT system may be arranged to determine stress within each layer having the known mechanical properties and strain within each area of interest such that the mechanical properties of the material at the areas of interest can be evaluated using the determined strain within the portion of material and the determined stress within the sensing layer.

Further, the actuator of the OCT system may be arranged to generate an acoustic wave in the material at the areas of interest and the OCT system may be arranged to measure a velocity of the acoustic wave within the material to determine a mechanical property of the material.

In accordance with a second aspect of the present invention, there is provided a method for characterising a material, the method comprising the steps of:

providing the material;

positioning first and second optical elements with first and second optical portions of an optical scanning system, respectively, at first and second surface areas of respective first and second regions of interest of the material, the first and second optical elements being at least partially transmissive for electromagnetic radiation, and being arranged such that respective reference radiation associated with the first and second optical elements is generated by reflection at interfaces of the first and second optical elements, respectively, and the first and second optical elements are arranged or positioned such that an optical path length difference between the reference radiation associated with the first optical element and electromagnetic radiation that interacted with the material of the first region differs from an optical path length difference between the reference radiation associated with the second optical element and electromagnetic radiation that interacted with the material of the second region;

optically coupling a detector to the scanning system;

directing electromagnetic radiation towards the first and a second regions through the first and second surface areas, respectively; and detecting the electromagnetic radiation received by the optical portions of the scanning system.

The first and second surface areas may be directly adjacent surfaces or may be spaced apart from each other. Further, the first and second regions may be directly below the first and second surface areas, respectively.

In addition, the first and second optical elements may be joined elements or may be separate elements that may or may not be spaced apart.

The first and second optical portions of the scanning system may be provided in the form of first and second scanning heads in use positioned at the first and second optical elements, respectively, to receive electromagnetic radiation that has interacted with the material at the first and second areas of interest. Alternatively, the OCT system may comprise a scanning system, such as a single scanning mirror, and may be arranged such that electromagnetic radiation is directed (for example via a beam splitter and a mirror) to the first and second optical portions, which may comprise suitable optical lenses.

The method may further comprise positioning the first and second optical portions of the scanning system at the first and second optical elements, respectively, to receive electromagnetic radiation that has interacted with the material of the first and second regions of the material, respectively.

The first and second optical elements may be separate from the first and second optical portions of the scanning system. In this case, the step of positioning first and second optical elements with first and second portions of an optical scanning system, respectively, may comprise positioning the first and second optical elements at first and second surface areas of respective first and second regions and positioning the first and second optical portions at the first and second optical elements, respectively.

Alternatively, the first and second optical elements may form parts of, or may be joined with the first and second optical portions of the scanning system, respectively.

The step of positioning a first and a second optical element at the first and second surfaces, respectively, may be conducted such that the first and second optical elements contact the respective surface areas or are spaced apart from the surface areas.

In one specific embodiment the method comprises directing both the reference radiation and the electromagnetic radiation that interacted with the material of the first region and also both the reference radiation and the electromagnetic radiation that interacted with the material of the second region such that they propagate along a common optical path towards a detector.

The method may further comprise a step of forming OCT images associated with material at the first and second regions simultaneously using the electromagnetic radiation received by the first and second optical portions and detected by the detector.

The material may be one of a plurality of materials. For example, the material may comprise first and second materials that are separate (and may be otherwise different) and the first optical element may be positioned at a first surface area of the first material and the second optical element may be positioned at the second surface area of the second material.

In one specific example, the first material may for example be biological tissue of a patient and the second material may be a mirror that is stationary relative to the second optical element. It is then possible to determine a motion of the second material relative to the OCT system.

In one embodiment of the present invention, the method comprises evaluating a mechanical property of the material in multiple areas of interest either in sequence or simultaneously.

The method may comprise applying a mechanical load to the first and second regions through the first and second surfaces, respectively, such as through the first and second optical element.

The method may further comprise determining strain within a portion of the material such that the mechanical property of the material can be evaluated using the determined strain within the portion of material at the first and second regions of interest.

The method may comprise determining stress within a sensing layer at or of each optical element; the sensing layers having known mechanical properties and being positioned between a portion of each optical element and the respective region of interest. The method may comprise determining stress within each sensing layer upon application of a suitable load. The may further comprise determining strain within each region of interest such that the mechanical properties of the material at the areas of interest can be evaluated using the determined strain within the portion of material and the determined stress within the sensing layer.

Further, the method may comprise generating an acoustic wave in the material at the regions of interest and the OCT system and measuring a velocity of the acoustic wave within the material to determine a mechanical property of the material.

BRIEF DESCRIPTION OF THE DRAWINGS

The present invention will now be described, by way of example only, with reference to the accompanying drawings, in which.

DETAILED DESCRIPTION OF SPECIFIC EMBODIMENTS

Figure 1:
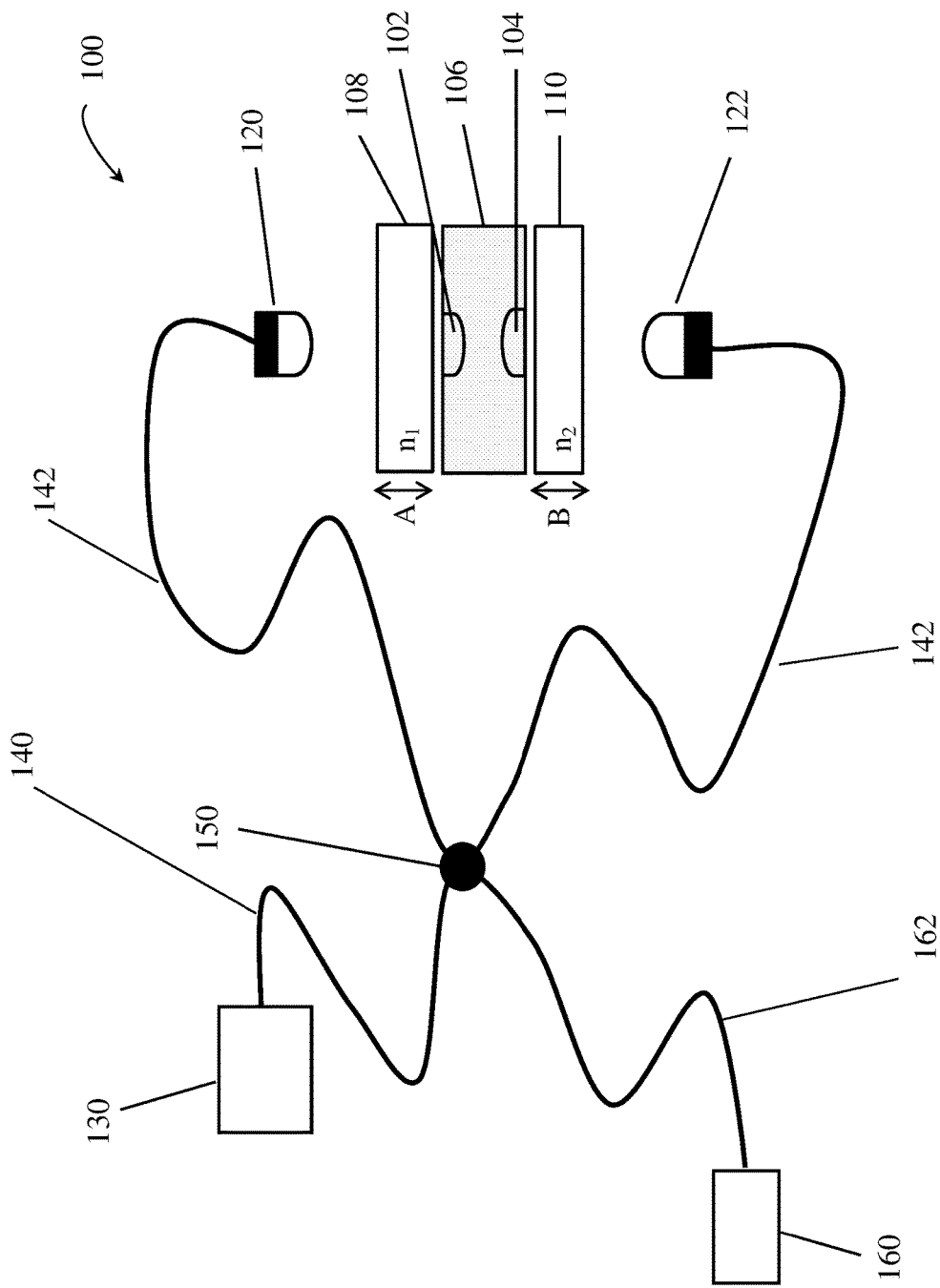
FIG. 1 shows a schematic representation of an OCT system in accordance with an embodiment of the present invention.

Embodiments of the present invention relate to a system and a method for characterising simultaneously a region of a single material or multiple materials and/or at multiple areas of interest using OCT.

The material may be a biological material, such as biological tissue. However, non-biological materials are also envisaged.

The OCT system in accordance with embodiments of the present invention comprises first and second optical elements, first and second scanning heads, and a detector that is optically coupled to the first and second scanning heads. The first and second optical elements are positioned at first and second areas of interest, respectively and are transmissive for electromagnetic radiation that is directed through the first and second optical elements.

The OCT system comprises a scanning system that may comprise first and second scanning heads or first and second optical portions to which electromagnetic radiation is directed from a scanning arrangement. The first and second scanning heads or the first and second optical portions are positioned at the first and second optical elements (typically spaced apart from the optical elements by a distance in the range of 0.5-30 mm), respectively, to direct electromagnetic radiation and receive electromagnetic radiation through respective optical elements. A portion of the electromagnetic radiation that is directed towards the first and second areas of interest is reflected at the interfaces of or at the respective optical elements to form respective reference radiation.

In a first embodiment of the present invention the first and second optical elements are further arranged such that an optical path length of electromagnetic radiation through a portion of the first optical element to an interface of or at the first optical element differs from that through a portion of the second optical element to an interface of or at the second optical element, whereby respective reference radiations having respective optical path lengths are generated.

In an alternative second embodiment of the present invention the optical elements are arranged or positioned such that an optical path length of electromagnetic radiation that interacted with the material at the first optical element differs from that of an optical path length of electromagnetic radiation that interacted with the material at the second optical element.

The OCT system comprises a source of electromagnetic radiation. The source is optically coupled to the scanning system that may comprise first and second scanning heads or first and second optical portions to which electromagnetic radiation is directed from a "central" scanning arrangement. The electromagnetic radiation emitted by the source is distributed between the first and second scanning heads using an optical fibre coupler or some other form of beam splitter.

The OCT system is further arranged such that reference radiation associated with each area of interest and the electromagnetic radiation that has interacted with the respective area of interest propagate along a single common path.

The electromagnetic radiation received by the detector from the first and second scanning heads is used to form an OCT image of the respective material at the first and second areas of interest. The optical path lengths differences between the reference radiation and the electromagnetic radiation that interacted with the material at the respective areas of interest determine the depth position of features of the first and second OCT images. The described optical properties of the first and second optical elements and optical path lengths differences are chosen such that the respective electromagnetic radiation and respective reference radiation received by the first and second scanning heads can be directed along a common optical path without significant overlap. For example, the OCT systems may have an imaging depth of one to a few millimetres, such as 1-5, 1-2, 1-3, or 1-2 millimetres. To avoid the overlap between the first and second OCT images, the OCT system is arranged such that the optical path length difference between the electromagnetic radiation that interacted with the material and the respective reference radiation associated with the first area of interest differs by more than 1-5, 1-2, 1-3, or 1-2 millimetres from the optical path length difference between the electromagnetic radiation that interacted with the material and the respective reference radiation associated with the second area of interest.

Further, the OCT system typically is arranged such that that the optical path lengths between both the electromagnetic radiation that interacted with the material and the respective reference radiation associated with the first area of interest differs by more than an imaging range (a few millimetres, such as 1-5, 1-2, 1-3, or 1-2 millimetres) of the OCT system from millimetres from the optical path lengths of both between the electromagnetic radiation that interacted with the material and the respective reference radiation associated with the second area of interest.

In addition, more than one material may be analysed simultaneously. For example, a first material may be a material of interest, such as biological tissue of a patent (in-vivo) and the second material may be a reference material, such as a reference mirror that is stationary relative to the second optical element. The first optical element may be positioned at surface of the biological tissue and the second optical element may be positioned at the reference mirror. It is then possible to determine a motion of the second material relative to the OCT system.

The OCT system in accordance with embodiments of the present invention will now be described in more detail with reference to the Figures.

Referring to FIG. 1, there is shown a schematic representation of an OCT system 100 for characterising two areas of interest 102 and 104 of a material 106 in accordance with the first embodiment of the present invention.

In this particular example, a first optical element 108 is positioned at the first area of interest 102 of the material 106 and a second optical element 110 is positioned at the second area of interest 104 of the material 106.

The OCT system 100 comprises two scanning heads 120 and 122. Each scanning head 120, 122 is coupled to an optical fibre from a Michelson interferometer (not shown) of the OCT system 100 and comprises a collimator, a scanning mirrors (e.g. galvanometer or MEMS-based mirrors) to deflect the beam in 2 dimensions across the surface of the material at the region of interest.

The first scanning head 120 is positioned at the first optical element 108 to receive electromagnetic radiation that has interacted with the first area of interest 102 of the material 106. The second scanning head 122 is positioned at the second optical element 110 to receive electromagnetic radiation that has interacted with the first area of interest 104 of the material 106.

A source of electromagnetic radiation 130 is optically coupled to the first and second scanning heads 120, 122 by means of optical fibres 140 and 142. The electromagnetic radiation emitted by the source 130 is distributed between the first scanning head 120 and the second scanning head 122 by means of an optical fibre coupler 150.

The electromagnetic radiation received by the first and second scanning heads 120, 122 propagates along a common optical fibre 162 towards the detector 160.

In this example, the optical elements 108 and 110 have thicknesses (A and B) and refractive indices ($n_1$ and $n_2$) selected such that the optical path length of the electromagnetic radiation through the first optical element 108 differs from that through the second optical element 110 by more than imaging depth of the OCT image of the material under test, in this example by more than 1 to 3 mm.

Alternatively, the optical elements 108 and 110 may also each comprise at least two layers having different refractive indices such that an interface is formed between two adjacent layers of each optical element at which electromagnetic radiation is reflected to form reference radiation. This embodiment will be described in more detail further below with reference to FIG. 3.

The first and second optical elements comprise a suitable glass material, but may alternatively also comprise a suitable polymeric material.

It will also be appreciated by a person skilled in the art that alternatively the optical elements may have the same thicknesses and different refractive indices, or may have different thicknesses and the same refractive indices. The optical elements 108, 110 and the scanning heads 120, 122 are illustrated as separate components. In a variation of the described embodiment the optical elements 108, 110 may also be joined to, or may form a part of, the scanning heads 120, 122.

Figure 2:
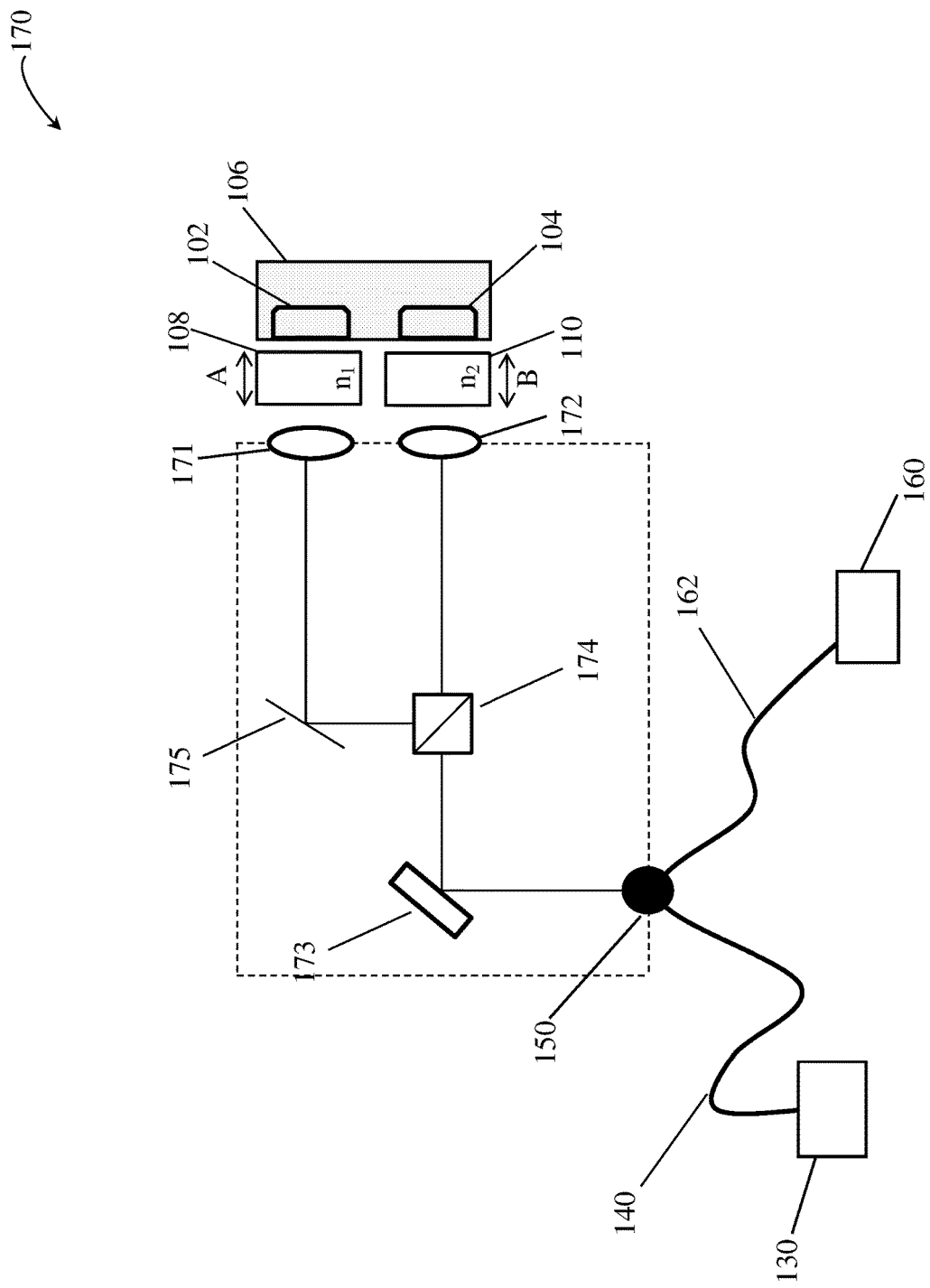
FIG. 2 shows a schematic representation of an OCT system in accordance with another embodiment of the present invention.

FIG. 2 illustrates an OCT system 170, which is a variation of the OCT system 100 illustrated in FIG. 1 and like components are given like reference numerals. The OCT system 170 has first and second optical portions, which are provided in the form of first and second lenses 171 and 172. The OCT system 170 has a single scanning mirror 173, which receives electromagnetic radiation from a Michelson interferometer of the OCT system 170 and directs electromagnetic radiation to the lenses 171, 172 via beam splitter 174 and mirror 175.

The scanning mirror 173, the lenses 171, 172, the beam splitter 174 and the mirror 175 may be positioned in a housing, which may be small and light enough to be handheld.

The optical elements 108, 110 and the optical portions heads 120, 122 of the scanning system are illustrated as separate components. In a variation of the described embodiment the optical elements 108, 110 may also be joined to, or may form a part of, the optical portions 120, 122, which may also be joined together.

The OCT systems 100, 150 may be used for evaluating a mechanical property of a material. The material may be a biological material, such as biological tissue or a biomaterial. However, non-biological material is also envisaged such as silicone material that is typically used for replicating the form and structure of biological soft tissue in the medical field.

The mechanical property typically relates to the elasticity of the material. Specifically, the elasticity may relate to a Young's modulus of the material. The Young's modulus is representative of the stiffness of the material. In the medical field, it has been known that abnormalities such as diseased tissue may alter the elasticity of biological tissue. For example, cancerous tissue typically are "stiffer" than surrounding healthy soft tissue. However, the mechanical property measured could also be viscoelasticity, anisotropy or poroelasticity.

The OCT systems 100, 170 in accordance with one embodiment of the present invention comprises a PZT based piezoelectric actuator (not shown) for applying a load to the material at the first and second areas of interest. It will be appreciated by a person skilled in the art, however, that alternatively a load may be applied to the material at the areas of interest using other means, such as manually, photothermal using for example thermal energy from laser absorption, acoustic of ultrasonic means.

Further, the OCT systems 100, 170 comprises sensing layers (not shown) positioned at respective optical elements having known mechanical properties. In this embodiment the sensing layers are formed from a silicone material. Alternatively, the layers of the first and second optical elements, such as the layers 304, 306, 312 and 310 can be used as sensing layers.

The OCT systems 100, 170 is arranged to determine stress within each sensing layer having the known mechanical properties and strain within each area of interest such that the mechanical properties of the material at the areas of interest can be evaluated using the determined strain within the portion of material and the determined stress within the sensing layer.

Further, an actuator may be arranged to generate an acoustic wave within the material at the areas of interest and the OCT system is arranged to measure a velocity of the acoustic wave within the material to determine a mechanical property of the material.

It will be appreciated by a person skilled in the art that the device has applications not only in the medical field, but also in various other fields including for example robotics and the food industry. The mechanical property may be evaluated for any suitable material that is compliant. For example, in the food industry, the device may be used to determine the ripeness of food. Further, the device may be used in quality control applications and for material processing.

Figure 3:
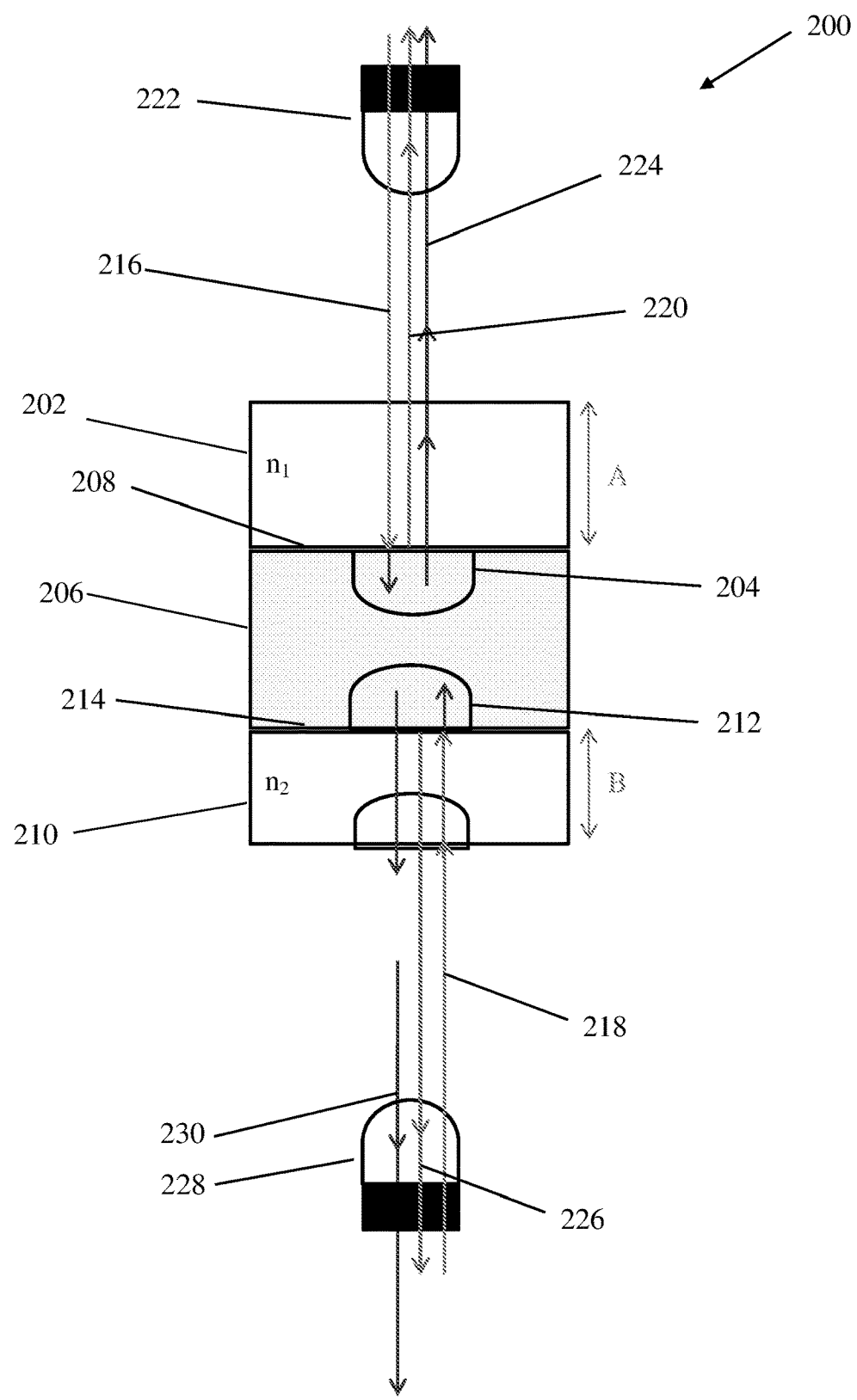
FIG. 3 shows a schematic representation of a portion of an OCT system according to one embodiment of the present invention.

Referring now to FIG. 3, there is shown a schematic representation of a portion 200 of the OCT system in accordance with an embodiment of the present invention.

In this embodiment, a first optical element 202 has a contact surface for contacting a first surface area of interest 204 of a material 206, so as to form the interface 208. Similarly, a second optical element 210 has a contact surface for contacting a second surface area of interest 212 of the material 206, so as to form the interface 214.

Electromagnetic radiation 216 is directed through the first optical element 202 towards the first area of interest 204 of the material 206, and through the second optical element 210 towards the second area of interest 212 of the material 206.

A portion of the electromagnetic radiation 216 directed towards the first area of interest 204 is reflected at the interface 208 to form the reference electromagnetic radiation 220. The scanning head 222 receives electromagnetic radiation 224 that has interacted with the first area of interest 204 along with the reference electromagnetic radiation 220.

Similarly, a portion of the electromagnetic radiation 218 directed towards the second area of interest 212 is reflected at the interface 214 to form the reference electromagnetic radiation 226. The scanning head 228 receives electromagnetic radiation 230 that has interacted with the second area of interest 212, along with the reference electromagnetic radiation 226.

The first and second optical elements 202 and 210 have refractive indices ($n_1$ and $n_2$) and thicknesses (A and B) that are chosen such that such that the optical path length difference between the reference electromagnetic radiation 220 and the electromagnetic radiation 224 differs from the optical path length difference between the reference electromagnetic radiation 226 and the electromagnetic radiation 230 by more than the imaging depth of the OCT image of the material under test, such as more than 1, 2 or 3 mm.

The electromagnetic radiation 220, 224, 226 and 230, received by the scanning heads 222 and 228, respectively, are directed along a common path (not shown) to a detector (not shown) and detected radiation is used to form simultaneously two OCT images of the material at the first and second areas of interest 204, 212.

Figure 4:
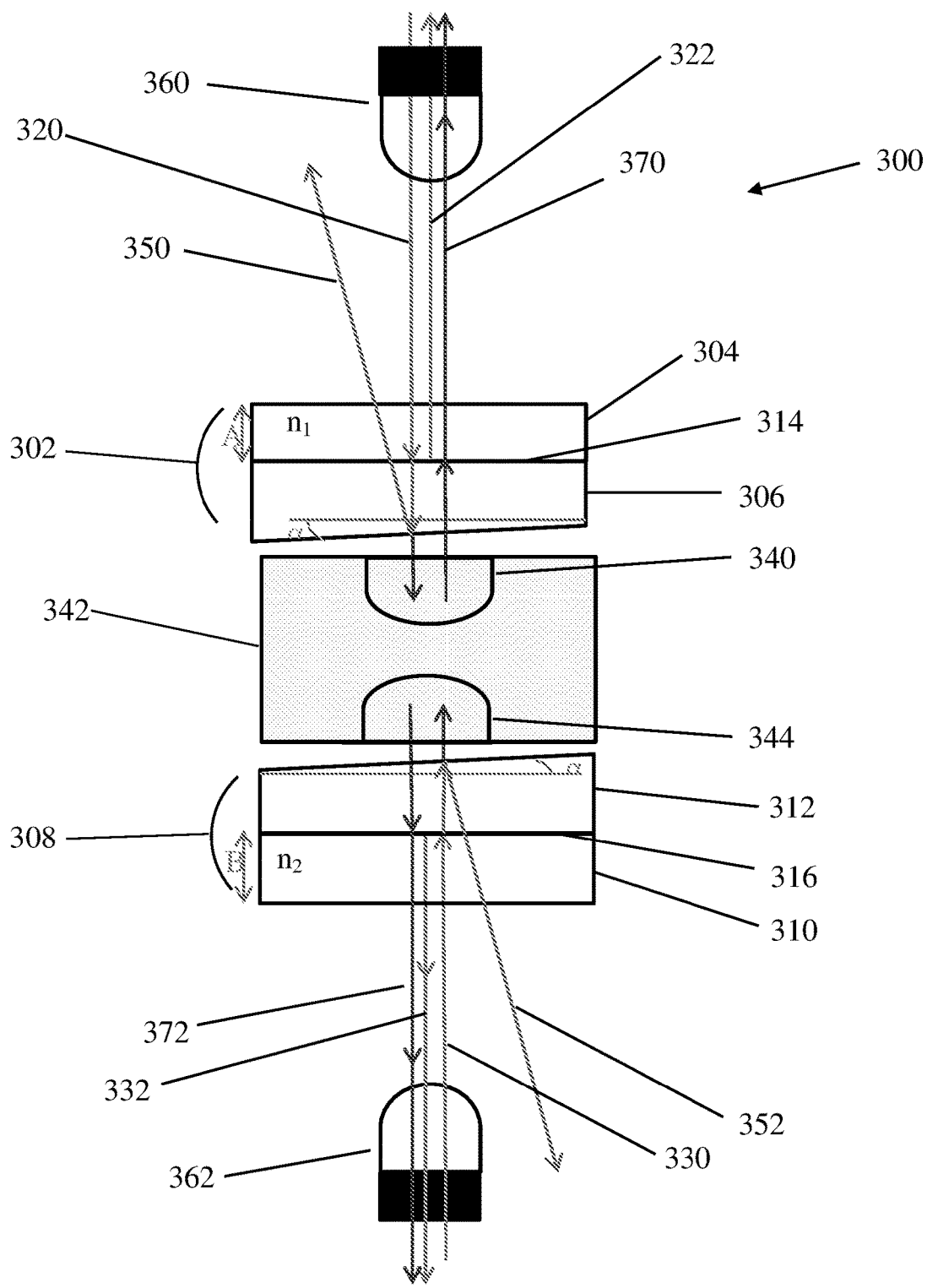
FIG. 4 shows a schematic representation of a portion of an OCT system according to another embodiment of the present invention.

Referring now to FIG. 4, there is shown a portion of the OCT system 300 according to another embodiment of the present invention.

In this embodiment, the first optical element 302 comprises a first layer 304 and a second layer 306 of a material that is transmissive for the electromagnetic radiation. The second optical element 308 comprises a first layer 310 and a second layer 312 of a material that is also transmissive for the electromagnetic radiation.

The two layers 304, 306 of the first optical element 302 have different refractive indices and form an interface 314. The two layers 310 and 312 of the second optical element 308 also have different refractive indices and form an interface 316.

A portion of the electromagnetic radiation 320 is reflected at the interface 314 of the first optical element 302 and forms the reference electromagnetic radiation 322. Further, a portion of the electromagnetic radiation 330 is reflected at the interface 316 of the second optical element 308 and forms the reference electromagnetic radiation 332.

In this embodiment, the first layer 304 and the first layer 310 have refractive indices and thicknesses selected such that the optical path length difference between the reference radiation 322 and the electromagnetic radiation 370 differs from the optical path length difference between the reference radiation 332 and the electromagnetic radiation 372 by more than the imaging depth of the OCT image of the material under test, such as more than 1, 2 or 3 mm.

The optical elements 302 and 308 have in this embodiment not a rectangular cross-sectional shape, but a surface at which the optical elements 302 and 308 contact the material is tilted by an angle α. This arrangement is chosen to avoid detection of electromagnetic radiation 350 and 352 that is reflected at an interface of the layers 306 and 312 with the material and could otherwise reduce a contrast of an OCT image that is being generated.

Figure 5:
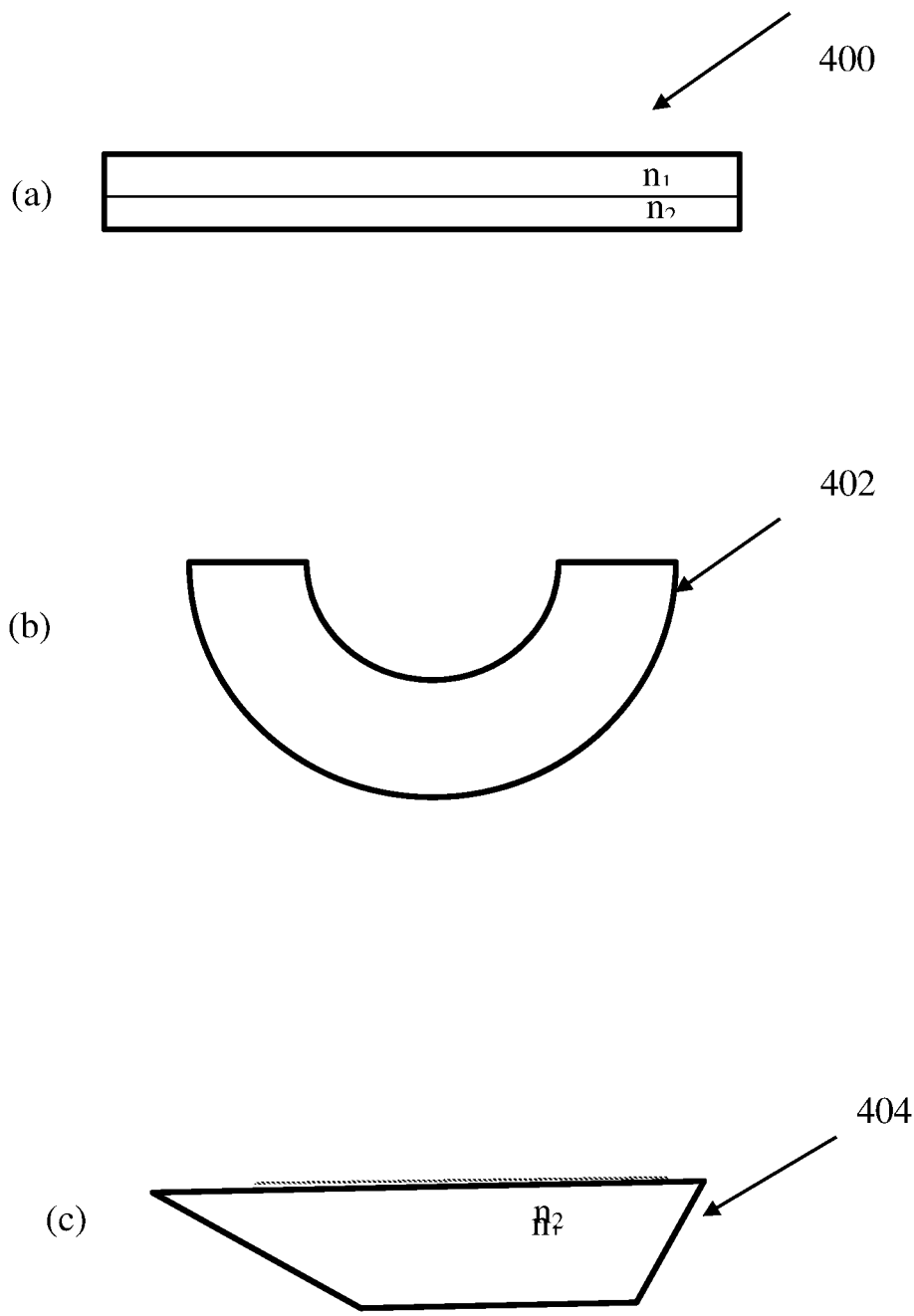
FIGS. 5 (a)-(c) shows optical elements in accordance with embodiments of the present invention.

Referring now to FIGS. 5 (*a*), (*b*) and (*c*), optical elements 400, 402 and 404 in accordance with embodiments of the present invention are now described.

The optical element 400 has a rectangular and generally flat shape and is similar to the optical elements 302 and 308 shown in FIG. 4, but does not have an inclined contact surface.

The optical element 402 is generally cup shaped and may for example replace the optical elements 202 or 210 shown in FIG. 3. A cup shaped optical element is particularly useful if the material is soft, such as biological tissue that may be positioned within the cup shaped optical element for OCT imaging. The optical element 402 is illustrated as having a uniform refractive index, but may alternatively also comprise cup shaped layers that have respective refractive indices and/or thicknesses, similar to the optical element 400 shown in FIG. 5 (*a*).

The optical element 404 has a prism or polygonal cross-sectional shape and comprises layers of respective refractive indices, but may alternatively all also comprise a material having a uniform refractive index. The optical element 400 may generally have any polygonal shape and may or may not comprise a contact surface that is inclined by an angle α. The optical element 400 may for example replace any one of the optical elements 302 or 308 shown in FIG. 4.

It will be appreciated by a person skilled in the art that any modifications and variations as would be apparent to a skilled addressee are determined to be within the scope of the present invention. For example, the characterisation of more than two areas of interest in a material simultaneously is envisaged. Further, the OCT system may comprise more than two scanning heads and the interconnections between the source, the first and second scanning heads, and the detector may be coupled by means of one or more devices similar to an optical splitter.

A person skilled in the art will appreciate that in a variation of the described first specific embodiment of the present invention the optical elements may have interfaces that are positioned such that there is essentially no optical path length differences phase difference between reference radiation associated with the first and second optical elements, but the first and second optical elements are positioned or otherwise structured such that the electromagnetic radiation that interacted with the material at the first optical element has an optical path length that is different to that of the electromagnetic radiation that interacted with the material at the second optical element. This variation relates to the second specific embodiment, which will now be described with reference to FIG. 6.

Figure 6:
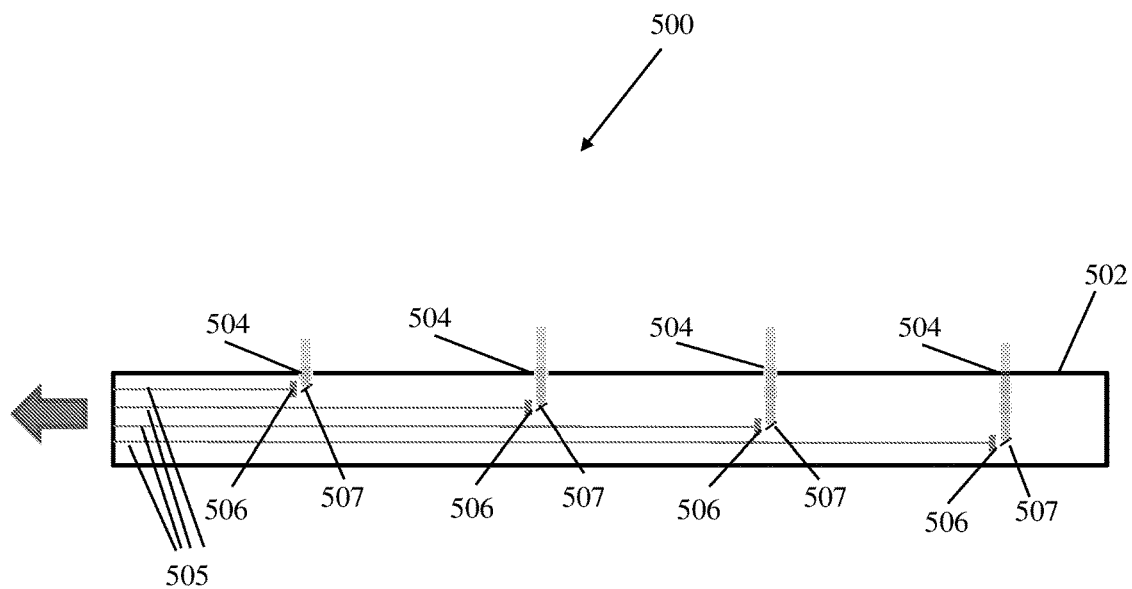
FIG. 6 shows a component of an OCT system in accordance with another embodiment of the present invention.

Referring now to FIG. 6, a component 500 in accordance with the second specific embodiment of the present invention is now described. The component 500 may for example function as an OCT endoscopic or needle. The component 500 comprises optical fibres that are coupled using fibre couplers (not shown) to form a common optical path to a detector. The component 500 comprises a body 502 that has a plurality of windows 504 that are transmissive for electromagnetic radiation. The optical fibres 505 are terminated at micro-lenses 506 at different positions along the length of the body 502. The component 500 further comprises mirrors 507 that are positioned to direct electromagnetic radiation between respective micro-lenses 506 and respective areas of interest. The micro-lenses 506 have interfaces that result in reflection of a portion of radiation that is directed to the micro-lenses 506 to generate reference radiation. The micro-lenses and the mirrors 507 are positioned at respective distances from respective windmills 504 whereby the electromagnetic radiation that interacted with the material has respective optical path lengths.

The component 500 may be used for OCT imaging for example by rotating or translating the body 502 within biological tissue. OCT images may be generated in the same manner as described above this reference to FIGS. 1 and 2.

A person skilled in the art will appreciate that in a variation of the embodiment described above with reference to a FIG. 6 the micro-lenses 506 and the mirrors 507 may have substantially the same spacings from the material, but the micro-lenses 506 may be structured to generate reference radiation that have respective optical path lengths, which relates to the embodiments described above with reference to FIG. 3 or 4.

Further, various additional variations are possible. For example, the first and second optical elements may be joined together or may be integrally formed and may be provided in the form of a single optical element (for example an optical element has a tapered thickness or refractive index profile along its length) and any number of optical portions may be positioned at, or joined to, that optical element.

The invention claimed is:

1. An optical coherence tomography (OCT) system for characterising first and second areas of interest of a material, the OCT system comprising:
    first and second optical elements in use positioned at the first and second surface areas, respectively, the first and second optical elements being at least partially transmissive for electromagnetic radiation;
    a scanning system having first and second optical portions, the first and second scanning portions being positioned at the first and second optical elements, respectively, to receive electromagnetic radiation that has interacted with the material within the first and second regions; and
    at least one detector optically coupled to the scanning system;
    wherein the first and second optical elements are arranged such that respective reference radiation associated with the first and second optical elements is generated by reflection at interfaces of or at the first and second optical elements, respectively, and the first and second optical elements are arranged or positioned such that an optical path length difference between the reference radiation associated with the first optical element and electromagnetic radiation that interacted with the first region differs from an optical path length difference between the reference radiation associated with the second optical element and electromagnetic radiation that interacted with second region.

2. The OCT system of claim 1 wherein the OCT system is arranged such that both the reference radiation and the electromagnetic radiation that interacted with the material associated with the first optical element and also both the reference radiation and the electromagnetic radiation that interacted with the material associated with the second optical element propagate along a common optical path towards the detector.

3. The OCT system of claim 1 wherein the first and second optical portions of the scanning system are provided in the form of first and second scanning heads that are positioned at the first and second optical elements, respectively, to receive electromagnetic radiation that has interacted with the material at the first and second areas of interest.

4. The OCT system of claim 1 wherein the first and second optical elements are arranged such that an optical length of a path of the electromagnetic radiation through at least a portion of the first optical element to an interface of or at the first optical element differs from that through at least of portion of the second optical element to an interface of or at the second optical element.

5. The OCT system of claim 1 wherein each of the first and second optical elements comprises at least two layers of a material having different optical properties and wherein the OCT system is arranged such that the electromagnetic radiation that is reflected at an interface between two of the at least two layers of each optical element forms respective reference radiation.

6. The OCT system of claim 1 wherein the first and second optical elements are arranged or positioned such that an optical path length of electromagnetic radiation that interacted with the material at the first optical element differs from that of the electromagnetic radiation that interacted with the material at the second optical element.

7. The OCT system of claim 1 wherein the first and second optical elements have a non-uniform thickness.

8. The OCT system of claim 1 wherein the OCT system is arranged to apply a mechanical load to the first and second areas of interest of the material.

9. A method for characterising a material, the method comprising the steps of:
    providing the material;
    positioning first and second optical elements with first and second optical portions of an optical scanning system, respectively,
    at first and second surface areas of respective first and second regions of interest of the material, the first and second optical elements being at least partially transmissive for electromagnetic radiation, and being arranged such that respective reference radiation associated with the first and second optical elements is generated by reflection at interfaces of the first and second optical elements, respectively, and the first and second optical elements are arranged or positioned such that an optical path length difference between the reference radiation associated with the first optical element and electromagnetic radiation that interacted with the material of the first region differs from an optical path length difference between the reference radiation associated with the second optical element and electromagnetic radiation that interacted with the material of the second region;
    optically coupling a detector to the scanning system;
    directing electromagnetic radiation towards the first and a second regions through the first and second surface areas, respectively; and detecting the electromagnetic radiation received by the optical portions of the scanning system.

10. The method of claim 9 wherein the first and second surface areas are directly adjacent surfaces.

11. The method of claim 9 wherein the first and second surface areas are spaced apart from each other.

12. The method of claim 9 wherein one of the first and second surface areas is directly below another one of the first and second surface areas, respectively.

13. The method of claim 9 wherein the first and second optical elements are joined elements.

14. The method of claim 9 wherein the first and second optical portions of the scanning system are provided in the form of first and second scanning heads in use positioned at the first and second optical elements, respectively, to receive electromagnetic radiation that has interacted with the material at the first and second areas of interest.

15. The method of claim 9 wherein the first and second optical elements are separate from the first and second optical portions of the scanning system and wherein the method further comprises positioning the first and second optical portions of the scanning system at the first and second optical elements, respectively, to receive electromagnetic radiation that has interacted with the material of the first and second regions of the material, respectively.

16. The method of claim 9 wherein the first and second optical elements may form parts of, or are joined with the first and second optical portions of the scanning system, respectively.

17. The method of claim 9 wherein the step of positioning a first and a second optical element at the first and second surfaces, respectively, is conducted such that the first and second optical elements contact the respective surface areas.

18. The method of claim 9 comprising directing both the reference radiation and the electromagnetic radiation that interacted with the material of the first region and also both the reference radiation and the electromagnetic radiation that interacted with the material of second region propagate along a common optical path towards a detector.

19. The method of claim 9 further comprising step of forming OCT images associated with material at the first and second regions simultaneously using the electromagnetic radiation received by the first and second optical portions and detected by the detector.

20. The method of claim 9 further comprising applying a mechanical load through the first and second regions through the first and second surfaces, respectively.

* * * * *